United States Patent [19]

Dormandy, Jr. et al.

[11] Patent Number: 4,819,637

[45] Date of Patent: Apr. 11, 1989

[54] SYSTEM FOR ARTIFICIAL VESSEL EMBOLIZATION AND DEVICES FOR USE THEREWITH

[75] Inventors: Ray H. Dormandy, Jr.; Julie D. Bell, both of South San Francisco, Calif.

[73] Assignee: Interventional Therapeutics Corporation, South San Francisco, Calif.

[21] Appl. No.: 92,079

[22] Filed: Sep. 1, 1987

[51] Int. Cl.⁴ ............................................ A61M 25/00
[52] U.S. Cl. .................................. 128/325; 128/344; 137/846; 604/283
[58] Field of Search ................................ 604/96–103, 604/241–243, 283, 247; 128/325, 344, 348.1; 137/846, 847

[56] References Cited

U.S. PATENT DOCUMENTS

| | | | |
|---|---|---|---|
| 3,504,699 | 4/1970 | Grise | 137/846 |
| 3,834,394 | 9/1974 | Hunter et al. | 128/325 |
| 4,191,185 | 3/1980 | Lemieux | 604/283 |
| 4,282,875 | 8/1981 | Serbinenko | 128/325 |
| 4,341,239 | 7/1982 | Atkinson | 137/847 X |
| 4,364,392 | 12/1982 | Strother et al. | 128/325 |
| 4,517,979 | 5/1985 | Pecenka | 128/325 |
| 4,559,043 | 12/1985 | Whitehouse et al. | 604/283 X |
| 4,682,978 | 7/1987 | Martin | 604/283 X |

Primary Examiner—Dalton L. Truluck
Attorney, Agent, or Firm—Flehr, Hohbach Test, Albritton & Herbert

[57] ABSTRACT

System for artificial vessel embolization comprising a catheter adapted to be inserted into the vessel and having a passage extending therethrough. A balloon delivery catheter is slidably mounted in the passage in the first named catheter. The balloon delivery catheter comprises a flexible elongate element having proximal and distal extremities. A detachable balloon is detachably secured to the distal extremity of the flexible elongate element. An adapter is carried by the proximal extremity of the flexible elongate element permitting inflation and deflation of the detachable balloon. The detachable ballon includes a cylindrical valve base having a bore extending therethrough and a self-sealing valve mounted on the valve base. The detachable balloon is mounted by a friction interference fit between the valve base and the distal extremity of the flexible elongate member. The size of the bore of the valve base is selected to provide the desired detachment force for the detachable balloon.

26 Claims, 2 Drawing Sheets

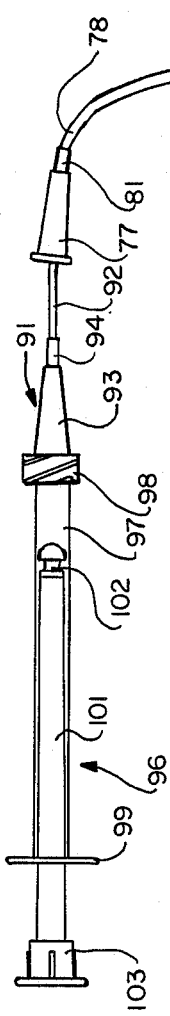
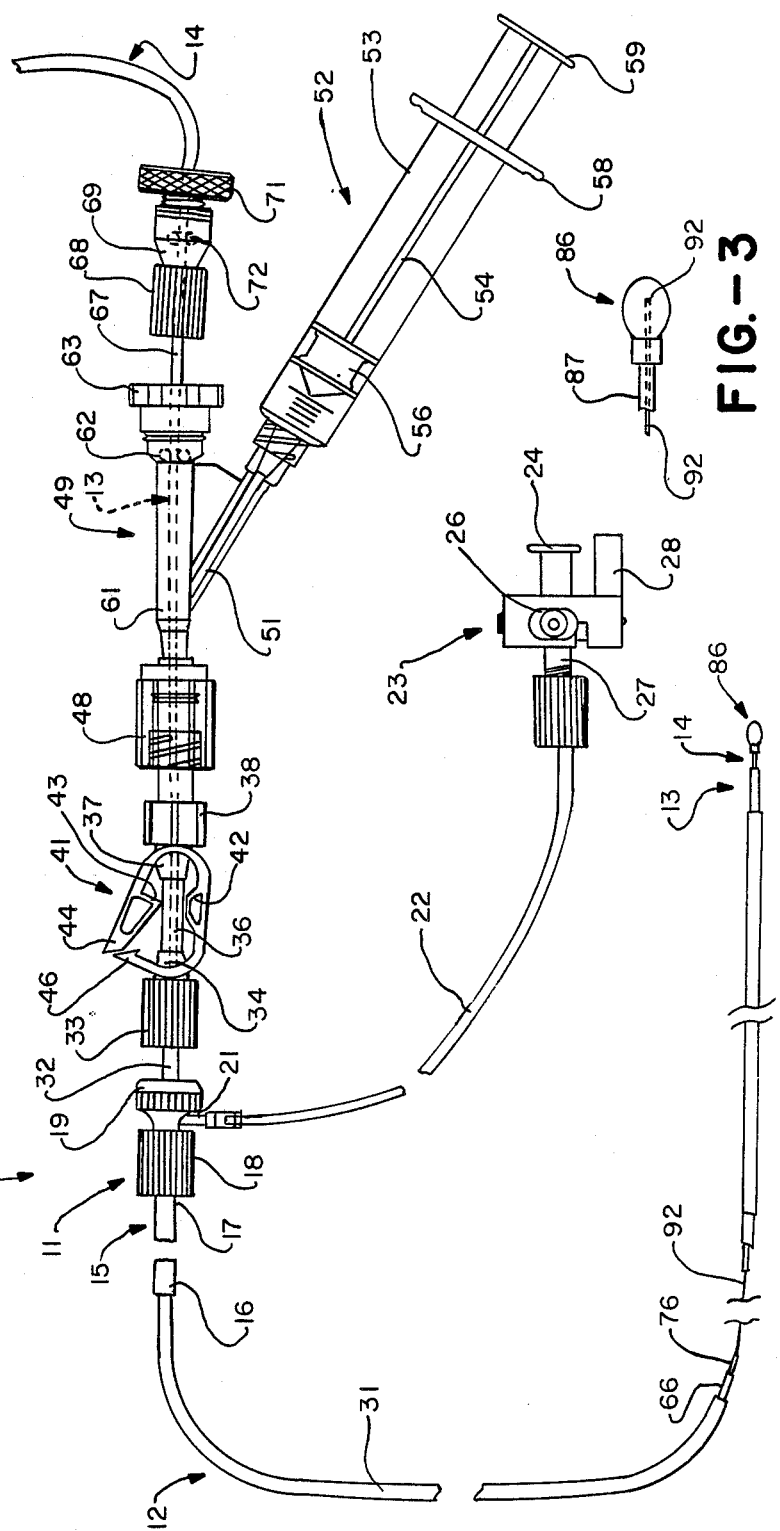
FIG.-1
FIG.-3

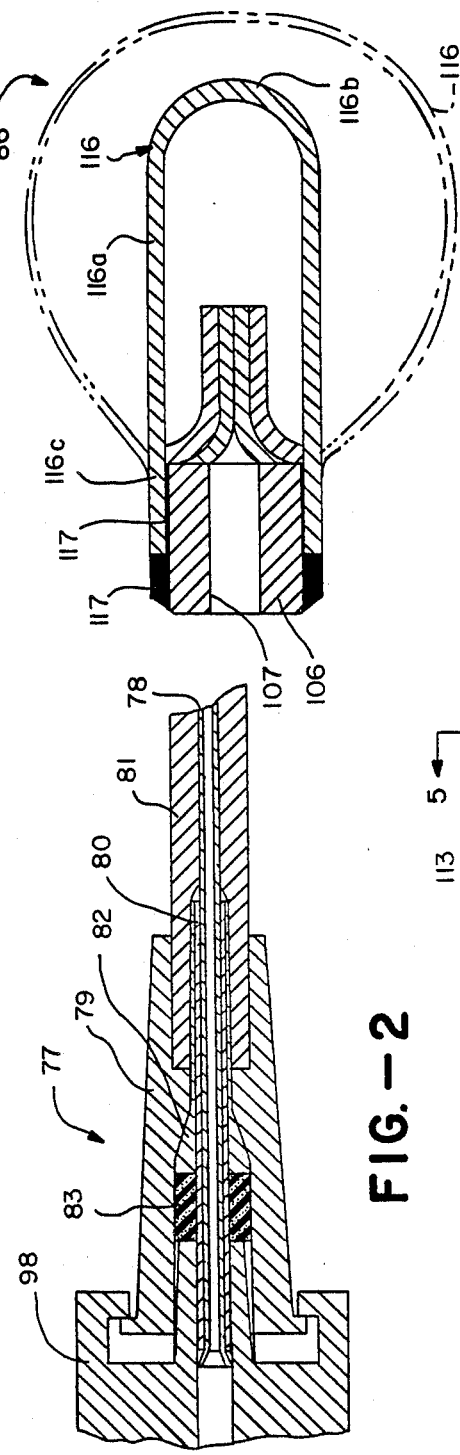
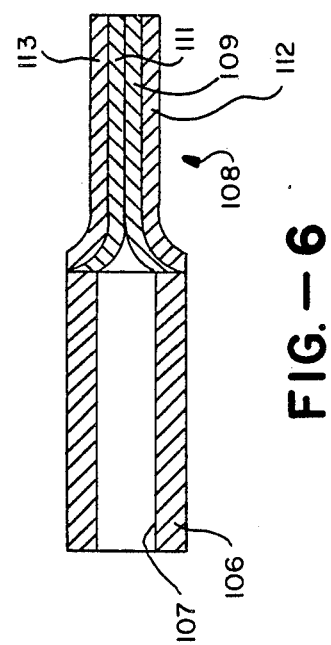
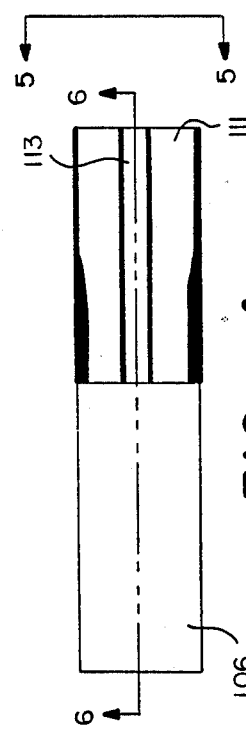
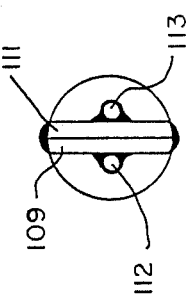

SYSTEM FOR ARTIFICIAL VESSEL EMBOLIZATION AND DEVICES FOR USE THEREWITH

This invention relates to a system and method for artificial embolization and devices for use therewith and more in particular to such a system utilizing detachable balloons.

Each year many people throughout the world will be diagnosed as having life-threatening saccular aneurysms of the cerebral arteries. Many people having such cerebral aneurysms will die or become disabled. Up to the present time, such aneurysms have been treated surgically with varying degrees of success. However, at least some degree of disability is associated with even the most successful and most conservative surgical procedures. Surgical treatment of vascular aneurysms continues to involve a high level of risk to the patient and results in a significant degree of surgical mortality and disability.

In the past there has been extensive research activity seeking means for treating such aneurysms that is less traumatic and which reduces or eliminates the need for surgical intervention. As early as 1962, it was suggested that a fixed (nondetachable) balloon catheter be used to artificially embolize the vessel leading to saccular aneurysms. Through medical developments, the nondetachable balloon evolved into a detachable balloon delivered on an intra-arterial flexible catheter and was used clinically as early as 1972. Subsequent clinical work has also used detachable balloons with gradually improving results. The invention describes a detachable balloon system which is capable of treating cerebral aneurysms through placement of the detachable balloon directly inside the aneurysmal sack thus preserving the original artery and blood flow.

Detachable balloons generally employ three main features; a shell to contain the inflation medium, a sealing mechanism to close the shell after detachment and means for maintaining attachment to the delivery means until detachment is desired. In the past balloon shells were fabricated from highly resilient elastic materials such as natural latex. While providing an adequate container an inflated balloon formed of latex becomes very hard and does not conform readily to surrounding tissue. The most commonly used sealing mechanisms employed in the past consisted of a simple elastic "string" tied around the neck of the balloon by each user. This has proven to be unreliable. Improved sealing mechanisms have been used but their complexity or size has prevented them from being used successfully in cerebral vessels. Cerebral blood vessels are usually fragile and injury to such vessels may have devastating results. In the past detachment of the inflated balloon required a high pulling force and the pulling force necessary to accomplish detachment was unpredictable. The results of inadvertent detachment often were devastating. Damage to the blood vessels and in particular to diseased vessel structures was frequent when a high pulling force was required.

There is therefore a need for a detachable balloon for artificial embolization which can be dependably placed inside the aneurysmal sack while reducing the trauma to surrounding tissue.

In general, it is an object of the present invention to provide a system for artificial vessel embolization and devices for use therewith.

Another object of the invention is to provide a system of the above character using a balloon delivery catheter with a novel detachable balloon.

Another object of the invention is to provide a system, and balloon delivery catheter of the above character in which detachable balloons are provided having different detachment forces.

Another object of the invention is to provide a system and balloon delivery catheter of the above character in which the balloon delivery catheter is relatively flexible.

Another object of the invention is to provide a system and introducer catheter of the above character of the above character having a smooth and uninterrupted interior flow passage through which the detachable balloon of the balloon delivery catheter can readily pass.

Another object of the invention is to provide a system and balloon delivery catheter of the above character in which the balloon delivery catheter may be preformed to provide a predetermined curve in the distal extremity.

Another object of the invention is to provide a system and balloon delivery catheter of the above character in which the balloon is formed of a biocompatible elastomer which provides a soft, compliant shell which at low and high inflation volumes reduces abrasion and stress of the walls of the vessel through which the balloon delivery catheter is introduced.

Another object of the invention is to provide a system and balloon delivery catheters of the above character in which migration of the balloon during detachment of the balloon from the catheter is minimized.

Another object of the invention is to provide a system and balloon delivery catheter of the above character in which a miniature valve construction is used which particularly lends itself to use in a detachable balloon.

Another object of the invention is to provide a system and balloon delivery catheter of the above character in which the balloon shell of the detachable balloon is secured to the miniature valve construction.

Another object of the invention is to provide a system and balloon delivery catheters with detachable balloons of the above character in which the balloons have preformed reinforcing ribs.

Another object of the invention is to provide a system and balloon delivery catheter of the above character in which the detachable balloons have a uniform concentric wall thickness, but which may have wall thicknesses which may vary longitudinally of the balloon.

Another object of the invention is to provide a system and balloon delivery catheter of the above character which utilize a detachable balloon having a balloon shell which has a uniform outside diameter but in which the inside diameter varies to provide a tapered wall thickness.

Another object of the invention is to provide a system and balloon delivery catheter of the above character in which the detachable balloon has a wall thickness which is the thinnest near the distal extremity of the balloon.

Another object of the invention is to provide a system and balloon delivery catheter of the above character in which a fitting is used which minimizes the dead space within the fittings.

Additional objects and features of the invention will appear from the following description in which the preferred embodiment is set forth in detail in conjunction with the accompanying drawings.

FIG. 1 is a plan view of a system incorporating the present invention.

FIG. 2 is an enlarged detail view of one of the fittings shown in FIG. 1.

FIG. 3 is an enlarged detail view of the detachable balloon shown in FIG. 1.

FIG. 4 is an enlarged view of the valve base with the miter valve mounted thereon utilized in the detachable balloon.

FIG. 5 is an end view looking along the line 5—5 of FIG. 4.

FIG. 6 is a cross-sectional view taken along the line 6—6 of FIG. 4.

FIG. 7 is a side elevational view of a detachable balloon mounted on the valve base with the miter valve incorporated therein.

In general, the system for artificial vessel embolization consists of an introducer catheter adapted to be inserted into the vessel. It has a flow passage extending therethrough. A balloon delivery catheter is slidably mounted in the flow passage in the introducer catheter. The balloon delivery catheter has a flexible elongate element with proximal and distal extremities. A detachable balloon assembly is detachably secured to the distal extremity of the flexible elongate element. Means is carried by the proximal extremity of the flexible elongate element permitting inflation and deflation of the detachable balloon. A cylindrical valve base having a flow passage extending therethrough is provided. A self-sealing valve is mounted on the valve base. The balloon assembly is attached to the delivery catheter by a friction fit between the valve base and the distal extremity of the flexible elongate member. The size of the bore and the valve base is selected to provide the necessary degree of fit in order to obtain the desired detachment interference force range for the detachable balloon. The balloon is constructed of a material which allows it to be soft, compliant and flexible to create minimum distortion to the blood vessel.

More in particular, the system 10 for artificial vessel embolization, consists of a dilator and sheath set 11, an introducer catheter set 12, a coaxial catheter set 13 and a balloon delivery catheter set 14. The dilator and sheath set 11 is of a suitable size as, for example, a 7.5 French sheath with appropriate dilator and consists of a flexible tubular member or sheath 15 which has a suitable length, as for example, 13 centimeters. It consists also of a dilator (not shown) which incorporates at its distal tip a suitable taper which allows it to navigate narrow openings in the human vessel as well as accommodate a flexible guide wire (not shown) to aid in placement. The sheath 15 is provided with a tapered distal extremity 16. The proximal extremity 17 is mounted in a knurled receptacle 18 which receives a threaded knob 19. The knob 19 is provided with a side port 21. A flexible tube 22 is connected to the side port 21 and also has a three-way stopcock valve assembly 23 connected thereto. The three-way stopcock assembly 23 is provided with inlet ports 24 and 26, an outlet port 27 and a valve member (not shown) which is positioned by a handle 28 to control the flow of fluid in inlet ports 24 or 26 to the outlet port 27. The inlet ports 24 and 26 are provided with Luer-type fittings and are adapted to be connected to suitable sources of supply for supplying a flushing liquid to either of the inlet ports 24 and 26. The dilator and sheath set 11 is provided with a self-sealing valve (not shown) in the knob 19. It serves to prevent any blood flow from the vessel of the patient when the sheath 11 remains in the vessel of the patient.

The introducer catheter set 12 which is introduced into the sheath set 11 consists of a flexible elongate member 31 which can have a suitable length as, for example, 120 centimeters. It can be a suitable size, as for example, 7.3 French. The proximal extremity 32 of the flexible elongate member 31 is secured to a compression fitting or coupling 33. The coupling 33 is adapted to be threaded onto an enlarged distal extremity 34 provided on a flexible link 36 formed of a suitable material such as polyurethane. The proximal extremity 37 of the flexible link 36 is connected to a Luer-type fitting 38.

A clamp 41 of a conventional construction is carried by the flexible link 36 and is provided with jaws 42 and 43 which are adapted to clamp therebetween the flexible link 36 by a clamping portion 44 being brought into engagement with the latching portion 46 of the clamp 41. The flexible link 36 has a flow passage (not shown) which provides a smooth uninterrupted surface passing through the clamp 41 and through which the coaxial catheter set 13, the balloon delivery catheter 14 and the detachable balloon 86 can be passed with ease when the clamp 41 is open. The clamp 41 remains open while the coaxial catheter 13 or the delivery catheter 14 extend through the flexible link. After the balloon delivery catheter 14 and the coaxial catheter 13 are withdrawn, the clamp 41 is closed to prevent any blood flow from the vessel of the patient.

The Luer-type fitting 38 is mounted in a rotating adapter 48 which forms a part of a two-arm adapter 49. The two-arm adapter 49 is provided with a side arm 51 having a Luer-type fitting which is adapted to have a syringe 52 mounted thereon. The syringe 52 can be of a suitable capacity, as for example, 5 cc's. The syringe 52 is provided with a cylinder 53 having a plunger 54 mounted for reciprocatory movement therein. A piston 56 is carried by the plunger 54. The syringe 52 is provided with outwardly extending flanges 58 formed on the cylinder 53 and a flat planar thumb portion 59 formed on the plunger 54 to permit the flanges 58 to be engaged by two fingers of one hand and the thumb portion 59 to be engaged by the thumb of the same hand. The two-arm adapter 49 is also provided with a central arm 61 which has an O-ring 62 mounted therein adapted to be moved into sealing engagement by a knurled knob 63.

The coaxial catheter set 13 of a suitable size such as 4 French is adapted to be introduced into the introducer catheter set 12 and consists of an elongate flexible member 66. The proximal extremity 67 of the flexible elongate member 66 is mounted in a knurled connector 68 which is threaded onto a fitting 69 having a knurled knob 71 threadedly mounted therein and adapted to engage an O-ring 72.

The balloon delivery catheter set 14 consists of a flexible elongate member 76 of a suitable size such as 2 French. A fitting 77 is mounted on the proximal end 78 of the flexible member 76. The fitting 77 is a modified type of fitting and as shown in cross-section in FIG. 2 consists of an outer shell or housing 79 formed of a suitable material such as plastic with a plastic or metallic tubular insert 80 mounted therein. The shell or housing 79 is bonded to the tubular insert 80 and to a reinforcing or strain relief tube 81 by an epoxy 82. An annular seal 83 of a soft sponge material such as polyurethane is provided in the shell or housing 79. As will be noted, the proximal extremity of the insert 80 extends beyond the proximal extremity of the shell 79. As can be seen the insert 80, the epoxy 82 and the sponge material 83 all occupy space which normally would be void when the fitting 77 is connected to a mating fitting as, for example, a fitting on a syringe.

A detachable balloon assembly 86 is detachably mounted on the distal extremity 87 of the flexible elongate member 76 forming a part of the balloon catheter 14. Means is provided for venting and filling the balloon assembly 86 as hereinafter described. This means consists of a vent tube assembly 91. The vent tube assembly 91 is comprised of a tubular member 92 formed of a material suitable to resist collapse under suction such as stainless steel, fused silica or firm plastic. It is of a suitable size, as for example, having an outside diameter of 0.010 inches and a flow passage (not shown) extending therethrough having an internal diameter of 0.006 inches. A Luer-type fitting 93 is mounted on the proximal extremity of the tubular member 92 with a reinforcing sleeve 94.

A syringe 96 is provided which can be attached to the fitting 93 or, alternatively, to the fitting 77. The syringe is provided with a cylindrical body 97 which has a female Luer-type fitting provided thereon which is adapted to receive the male-type fitting 93. The body 97 is provided with flanges 99. A plunger 101 is mounted within the cylindrical body 97 which carries a piston 102. The plunger 101 is provided with a knob or thumb portion 103 which is adapted to be engaged by the thumb of the hand while the fingers of the hand engage the flanges 99 to cause movement of the plunger 101 within the cylindrical body 97.

Operation and use of the devices comprising the system for artificial vessel embolization may now be briefly described as follows. Let it be assumed that it is desired to introduce a balloon delivery catheter 14 into the arterial vessel of the patient. This can be accomplished by making a puncture with a needle (not shown) into an artery of the patient as, for example, the femoral artery. As soon as this has been accomplished, a suitable guidewire (not shown) is used, as for example, a flexible guidewire having a diameter of 0.038 inches and a suitable length as, for example, 40 centimeters. As soon as the guidewire has been introduced through the needle, the puncture needle can be withdrawn over the guidewire. The sheath or dilator set 15 (dilator not shown) is then advanced over the guidewire into the femoral artery.

After the dilator and sheath 15 has been properly positioned, the guidewire and dilator but not the sheath 15 can be withdrawn. At that time, the self-sealing valve in the knob 19 closes to prevent the escape of blood from the arterial vessel. The 7.3 French introducer catheter 12 with a 5 French guide catheter (not shown) mounted thereon are inserted through the knob or valve member 19 of the sheath 11.

The introducer catheter which can typically have a length under 120 centimeters is designed so it can be advanced through restrictive bends, as for example, in the carotid artery. The guide catheter (not shown) which possesses a tapered tip, aids in positioning of the introducer catheter 12. The guide catheter can be utilized for introducing a radiopaque solution to facilitate visualization of the artery as the catheter 12 is being advanced.

Typically the guide catheter and the introducer catheter 12 can be advanced simultaneously up to a point beyond the aortic arch. After the introducer catheter 12 has been properly positioned, the guide catheter can be withdrawn and the clamp 41 closed to compress the flexible link 36 to prevent the escape of blood from the arterial vessel.

The 4 French coaxial catheter 13 and the 2 French balloon delivery catheter 14 are prepared for introduction outside of the body of the patient. The side arm adapter 49 is separated if it already is not separated from the flexible link 36 at the Luer fitting 38. The 5 cc syringe 52 is removed and filled with a saline solution and secured to the side arm 51. The syringe 52 is operated to flush the side arm 51 as well as the central arm 61 of the two-arm adapter 49. The coaxial catheter 13 is then introduced through the central arm 61 by rotating the knob 63 to decompress and open the O-ring 62. The coaxial catheter 13 is then passed through the central arm 61 so that it extends approximately 2 cm beyond the distal extremity of the two arm adapter 49. The delivery catheter 14 i then introduced through the coaxial catheter 13 by rotating the knob 71 to decompress and open the o-ring 72. The delivery catheter 14 is then inserted into fitting 69 and advanced for a distance so that it extends approximately 5 centimeters beyond the distal extremity of the coaxial catheter 13. The 1 cc syringe 96 is then taken and attached to the Luer-type fitting 77 and the plunger 101 is operated to introduce a saline solution through the delivery catheter 14. After the delivery catheter 14 has been flushed with a saline solution, a detachable balloon 86 is then taken and the distal extremity of the delivery catheter 14 is carefully inserted into the detachable balloon 86 so that it enters and extends completely through the internal valve (hereinafter described) of the detachable balloon 86. The detachable balloon can then be tested by inflating it with a saline solution from the syringe 96. After the balloon has been tested, the balloon is deflated by removing saline solution from the same and both the coaxial catheter 13 and the delivery catheter 14. The coaxial catheter 13 and the delivery catheter 14 with the balloon 86 are withdrawn to the tip of the two arm adapter 49. The knob 63 is then tightened to hold the coaxial catheter in place. The knob 71 is then tightened to hold the delivery catheter in place.

During this procedure the clamp 41 on the introducer catheter 12 remains closed. The two arm adapter 49 can then be secured to the proximal fitting 37 carried by the flexible link 36. The coaxial catheter 13 can then be unlocked by rotation of the knob 63 and similarly, the clamp 41 can be opened to permit the coaxial catheter 13 and the delivery catheter 14 with its detachable balloon 86 on its tip to be advanced through the flexible link 36 and past the clamp 41.

The knob 71 remains tightened while the coaxial catheter 13 and delivery catheter 14, with balloon 86 attached are advanced through the introducer catheter 12. The knob 71 can be loosened to allow the delivery catheter 14 to be advanced independently of the coaxial catheter 13.

In this way the coaxial catheter 13 and the delivery catheter 14 can be advanced through the arterial vessel to the desired location. The advancement can be watched under x-ray by observation of the radiopaque balloon valve base 106, the radiopaque delivery catheter 14 or by introducing a radiopaque medium into the balloon 86.

After the balloon 86 has been properly positioned, let it be assumed that it is desired to exchange the radiopaque medium with a suitable solidifying agent or material to ensure that the balloon serves as a permanent embolus. A suitable solidifying agent is HEMA gel, a water soluble synthetic hydrogel comprised of a homogeneous monomer 2-hydroxyethyl methyacrylate blended with a crosslinking agent polyethylene glycol dimethyacrylate. In order to accomplish this, the filling syringe 96 is removed from the fitting 77 and the vent tube assembly 91 is introduced through the fitting 77. The vent tube 92 is advanced through the delivery catheter 14 until it is in reasonably close proximity to the balloon 86. A suitable syringe, such as a syringe 96 is filled with the solidifying material and then secured to the fitting 93. As the syringe is operated, the solidifying medium will be introduced through the vent tube 92 and into the balloon 86 and then outwardly from the balloon in the annular passage formed between the vent tube 92 and the interior of the delivery catheter 14. This procedure is continued until all of the radiopaque liquid which in the balloon and in the delivery catheter 14 is discharged through the fitting 77 outside of the body of the patient. Once it has been established that the space within the balloon has been filled as well as the void space in the delivery catheter has been filled with the solidifying agent, the vent tube 92 can then be removed. As soon as the filling operation has been completed, the knob 63 on the two arm adapter 44 is tightened to hold the coaxial catheter 13 in place. The delivery catheter 14 can then be withdrawn by allowing it to withdraw from the balloon 86 and to permit the balloon 86 to become detached therefrom. As soon as this has occurred, the delivery catheter 14 and the coaxial catheter 13 as well as the introducer catheter 12 can be removed as a single unit. Alternatively, the introducer catheter 12 can remain in place if it is desired to place additional balloons in the body of the patient.

The construction of the detachable valves utilized with the system of the present invention can now be described in detail. The detachable balloon 86 is provided with a valve base 106 which is in the form of a tubular member which can have a suitable dimension such as an outside diameter of 0.038 inches and an inside diameter of 0.022 inches. It is formed of a suitable flexible material. It is also preferably provided with a material which is radiopaque under x-rays. To accomplish this, a silicone elastomer is utilized in which there is incorporated a suitable radiopaque agent such as barium sulfate in a suitable amount as, for example, approximately 9 to 11% and preferably approximately 10% by weight. The two materials are blended and extruded to form the valve base 106 shown in FIGS. 4, 6 and 7. The valve base 106 is cylindrical in form and is provided with a smooth cylindrical bore or flow passage 107 extending therethrough. A self-sealing mitre or duck bill valve 108 is provided. The duck bill valve 108 is formed from two sheets or vanes 109 and 111 of a silicone elastomer sheeting or other flexible material having a suitable thickness as, for example, 0.005 of an inch. The sheets 109 and 111 are cut to size and have a generally rectangular configuration. The side edges of the vanes 109 are fastened together by a suitable adhesive, preferably a silicone adhesive which has been pigmented to provide a color coding which identifies the detachment force which is provided by the valve base.

Tubular members or rods 112 and 113 are provided on the exterior surfaces of the vanes or sheets 109 and 111 and preferably are centrally disposed thereon. The rods 112 and 113 are also formed of a silicone material and are extruded with a suitable radiopaque agent such as the barium sulfate previously mentioned. The rods 112 and 113 are flexible and are secured to the vanes 109 and 111 by suitable means such as an adhesive. One end of the miter or duck bill valve 108 is then secured to one end of the valve base 106 by spreading and bending the vanes 109 and 111 apart so as to adapt to the passage 107. The vanes with the reinforcing rods 112 and 113 thereon are maintained in a bent configuration and are secured to one end of the valve base 106 by a silicone adhesive which is preferably pigmented to provide a color coding the same as used on the vanes which identifies the detachment force which is provided by the valve base. The bent configuration of the valve vanes provides a permanent yieldable closing force to the valve vanes 109 and 111. The use of the reinforcing rods 112 and 113 on the vanes 109 and 111 of the mitre or duck bill valve 108 provides pre-stressing for the vanes to provide a relatively continuous force to overcome any tendency of the valve vanes to remain open. The detachment force is primarily determined by the internal diameter of the flow passage 107 provided in the valve base 106 and by the elasticity of the material used to form the valve base 106.

A balloon shell 116 is provided which has been previously formed from a soft distensible silicone elastomer material that provides enhanced elongation and expansion characteristics. The balloon shell 116 has a wall thickness prior to expansion ranging from 0.005 to 0.008 of an inch. The balloon is provided with an elongate cylindrical portion 116a with a rounded tip 116b. Typically, the balloon shell 116 can have an uninflated diameter ranging from 2 mm to 0.085 mm. Typically the balloon shell is trimmed so it has a length of 0.215 of an inch and so that its open end can fit over the valve base 106 and be adhered to the valve base 106 by a silicone adhesive shown at 117. By way of example, the glued down portion 116c of the balloon can have a length of approximately 0.060 of an inch leaving a free length of approximately 0.155 of an inch in length. It should be appreciated that balloons of different free lengths can be provided as, for example, ranging from 0.100 of an inch to 0.350 of an inch. After the balloon shell 116 has been secured to the valve base 106, the valve base can be trimmed to a suitable length such as, for example, 0.060 of an inch as shown in FIG. 7 of the drawings. The balloon shell 116 inflates very uniformly as shown by the dotted lines 116 in FIG. 7 so that it inflates concentrically without offside or irregular expansion. By changing the length of the balloon shell 116, it is also possible to provide a balloon which inflates substantially spherically with a relatively short balloon and substantially cylindrically with a longer balloon. Different balloon shapes can be readily achieved by altering the composition of the silicone material utilized as well as varying the wall thickness while maintaining a concentric uniform wall in the balloon shell. The wall thicknesses can be varied so it decreases toward the distal extremity to provide a tapered configuration.

Should balloon shell rupture occur accidentally, the tapered configuration causes a tear in the balloon to propagate in a longitudinal direction as opposed to circumferentially. The longitudinal tear is advantageous because it does not generate balloon fragments which could be released into the vascular system and increasing the risk of stroke. The use of silicone elastomer for the balloon is in and of itself advantageous because it promotes tear propagation in response to stress as opposed to fragmentation or shattering of the material.

In certain applications of the invention it is desirable to have the balloon shell 116 formed of a material which is extremely distensible. For example, an expansion ratio of 8 to 10 can be obtained by utilizing a low durometer material. This material can be obtained by using a softer type of filler or a very homogenous filler with the silicone to provide high elongation at high tensile strength.

The detachable balloon which is shown in FIGS. 4-7 is typically used in connection with a 2 French delivery catheter having an outside diameter of 0.026 inches. The construction of the valve base 106 makes it possible to provide with relative ease detachable balloons with different detachment forces merely by varying the size of the bore 107 provided in the valve base 106. Different detachment forces may also be obtained by varying the elasticity of the material from which the valve base 106 is formed. In order to provide a consistent degree of friction between the valve base 106 and the smooth cylindrical outer surface of the distal tip of a predetermined diameter of the delivery catheter 14 a lubricant, preferably non-absorbing water-resistant and silicone-based, is supplied to the bore 107 of the valve base 106. This lubricant reduces the static friction or bonding between the delivery catheter 14 and valve base 106 and eliminates an abrupt withdrawal caused by static friction.

The valve bases 106 provided for use with such balloon catheters can have inside diameters ranging from approximately 0.022 inches for a low detachment force, approximately 0.015 inches for a high detachment force and 0.018 inches for a medium detachment force. The silicone material which is utilized for forming the valve base 106 is particularly suitable for use in providing valve bases with different detachment forces because the silicone material is extremely elastomeric and readily accommodates the necessary stretching to achieve the different detachment forces. By way of example, detachment balloons which are color coded blue can have a low detachment force, detachment balloons color coded orange can be a medium detachment force and detachment balloons color coded white can have a high detachment force.

The accurate fit of the valve base on the delivery catheter as well as the use of a lubricant in the valve base allows detachment of the balloon to occur in a smooth consistent motion, thus preventing dislodgement or migration of the balloon and delivery catheter away from the desired placement site in the vessel. Abrupt and unpredictable detachment is minimized.

The construction of the fitting 77 has several advantages. The proximal end 78 of the flexible member 76 passes completely through the fitting 77 without connectors or interruptions in the internal lumen. This increases the visibility of the opening of the proximal end 78 and reduces the possibility of air entering or remaining in the catheter during filling. The unoccupied volume in the fitting 77 is minimized which reduces the volume of saline solution which must be removed when a vent tube is not used during a fill material exchange. This makes it possible to ensure that the balloon itself as well as any lumen leading to the balloon is evacuated because of the decrease of void or unoccupied space in the fitting. It also makes it possible to decrease the time required for deflation of the balloon.

From the foregoing it can be seen that a system and method for artificial vessel embolization and devices for use therewith have been provided. The detachable balloon as described provides a non-operative, angiographically controlled, superselective technique of intravascular occlusion. In appropriate anatomical and hemodynamic situations, the detachable balloons may be used to embolize arteries, fistulae, vascular malformations, varicoceles, and aneurysms. In addition, the detachable balloon may also be used for the nonsurgical control of hemorrhage from certain traumatic, neoplastic or degenerative causes. In addition, the detachable balloons may provide assistance in the preoperative embolization of certain lesions to reduce blood flow to an area of interest. Although the detachable balloon has been described as being catheter guided to the desired site, it should be appreciated that if desired the balloon can be flow directed in a manner well known to those skilled in the art.

The base of the valve utilized in the detachable balloon is comprised of a radiopaque silicone which allows visualization in vivo and also provides a seal around the catheter during delivery. The valve base is designed to provide a specific release range when the balloon is used with the appropriate delivery catheter. As hereinbefore described, it can be seen that the detachable balloon is designed to be introduced to the body of a patient using a coaxial delivery system. The coaxial delivery system hereinbefore described allows the physician to flush the delivery catheter prior to placing the balloon on the end of the delivery catheter. The detachable balloon, partially filled with contrast medium, may be flow directed or catheter guided to the desired site of embolization. Angiography may be used to verify the placement of the balloon at the desired location. Inflation of the balloon using either contrast agents or polymerizing agents completes the occlusion of the vessel or lesion. Subsequent blood stasis, clotting and fibrous tissue growth encapsulate the balloon, thereby achieving permanent occlusion.

What is claimed is:

1. In a system for artificial vessel embolization, a catheter adapted to be inserted into the vessel and having a passage extending therethrough, a balloon delivery catheter slidably mounted in the passage in the first named catheter, the balloon delivery catheter comprising a flexible elongate element having proximal and distal extremities, the distal extremity having a smooth outer cylindrical surface of a predetermined diameter, a detachable balloon detachably secured to the distal extremity of the flexible elongate element and means carried by the proximal extremity of the flexible elongate element permitting inflation and deflation of the detachable balloon, the detachable balloon including a cylindrical valve base having a smooth surface cylindrical bore extending therethrough, a self-sealing valve mounted on the valve base, said detachable balloon being mounted by a friction interference fit between the valve base and the distal extremity of the flexible elongate member, the size of the bore of the valve base being selected to provide the desired detachment force for the detachable balloon and a lubricant disposed in the bore to reduce static friction between the valve base of the detachable balloon and the flexible elongate element.

2. A system as in claim 1 wherein said self-sealing valve means includes a duck-bill type valve having first and second curved sheet-like vanes and normally straight rod-like reinforcing members carried by the vanes and being bent from the normally straight position to place predetermined closing forces on the vanes.

3. A system as in claim 1 wherein said valve base includes a material which is radiopaque.

4. A system as in claim 1 wherein said detachable balloon is color coded to provide an indication of the detachment force for the detachable balloon.

5. A system as in claim 1 together with an introducer catheter and wherein said first named catheter is disposed in the introducer catheter.

6. A system as in claim 5 together with a sheath and wherein the introducer catheter is disposed in the sheath and means carried by the sheath permitting the introduction of a liquid between the sheath and the introducer catheter.

7. A system as in claim 6 together with means connected to the introducer catheter for introducing a liquid between the introducer catheter and the first named catheter.

8. A system as in claim 5 together with openable clamping means carried by the introducer catheter for clamping off the introducer catheter.

9. A system as in claim 8 wherein said introducer catheter includes a flexible link having a smooth-surfaced passage extending therethrough and wherein said clamping means is mounted on said flexible link.

10. A system as in claim 9 wherein said first named catheter and said delivery catheter extend through said smooth-surfaced passage of said flexible link.

11. A system as in claim 1 for use with a first fitting and wherein the proximal extremity of the flexible elongate element of the balloon delivery catheter is provided with a second fitting adapted to be connected to said first fitting, said second fitting including a shell having a space therein and means disposed within the space in the shell so that when the second fitting is connected to said first fitting there is substantially no unoccupied space in the second fitting.

12. A system as in claim 11 wherein said means disposed within the shell includes a cylindrical member.

13. In a detachable balloon for use in artificial vessel embolization, a cylindrical valve base having a smooth-surfaced cylindrical bore of a predetermined size extending therethrough, the valve base having a radiopaque material incorporated therein so as to make radiopaque material incorporated therein so as to make possible visualization of the valve base in the vessel, a self-sealing prestressed valve carried by the valve base for closing the bore in the valve base and an extensible balloon carried by the valve base, said self-sealing prestressed valve being in the form of a duck bill valve having formed first and second sheets, means binding the side edges of the sheets together, a reinforcing rod secured to each of the sheets and extending longitudinally of the bore, said rods being bent from a normally straight condition to place a permanent yieldable closing force on the sheets and means for securing the sheets to the valve base.

14. A detachable balloon as in claim 13 wherein said valve base and said balloon are formed of a silicone elastomer.

15. A detachable balloon as in claim 13 wherein the size of the bore is changed to change the detachment force for the detachable balloon.

16. A detachable balloon as in claim 13 wherein said valve base is color coded to indicate the detachment force required for the detachable balloon.

17. A detachable balloon as in claim 14 wherein the silicone elastomer is compounded with minimal filler to provide a soft, high elongation compliant balloon shell with a low tensile set and substantially reduced fragmenting or shattering characteristics.

18. In a Luer-type fitting assembly, a flexible elongated element having a flow passage therein and having a proximal extremity a female Luer-type fitting mounted on the proximal extremity of the flexible elongate member so that it extends through the female Luer-type fitting, the female Luer-type fitting having a shell with a space therein through which the flexible elongate member extends, a male Luer-type fitting engaging the female Luer-type fitting and having a protrusion extending into a portion of the space in the shell, the protrusion having a flow passage which receives the proximal extremity of the flexible elongate member and means filling the remaining portion of the space in the shell so that there is a minimum of unoccupied space in the fitting assembly when the female and male Luer-type fittings are interconnected.

19. A fitting as in claim 18 wherein the filling means includes a cylindrical element having a flow passage therein.

20. A kit apparatus for use in artificial vessel embolization comprising a catheter adapted to be inserted into the vessel and having a passage extending therethrough, a balloon delivery catheter comprising a flexible elongate element having proximal and distal extremities, the distal extremity having a smooth outer cylindrical surface of a predetermined diameter, and a plurality of detachable balloons adapted to be detachably secured to the distal extremity of the flexible elongate element, each of the detachable balloons including a cylindrical valve base having a smooth surfaced cylindrical bore extending therethrough and a self-sealing valve mounted on the valve base, said detachable balloons being adapted to be mounted by friction interference fit between the valve base and the distal extremity of the flexible elongate member, each valve base of said detachable balloons having a bore size differing from the bore size of the valve base of the other detachable balloons so that by selecting a detachable balloon having a valve base of a predetermined bore size, the detachment force for the detachable balloon can be selected.

21. A kit apparatus as in claim 20 wherein each of said detachable balloons is color coded to identify the detachment force which is provided by the valve base of the detachable balloon.

22. A kit apparatus as in claim 20 wherein the valve base of each of the detachable valves is formed of an elastomer.

23. A kit apparatus as in claim 20 wherein the valve base of each of the detachable valves has a radiopaque agent incorporated therein.

24. A kit apparatus as in claim 20 wherein a substantially non-absorbing water resistant lubricant is provided in the bore of each of the valve bases of each of the detachable balloons.

25. A kit apparatus as in claim 24 wherein the valve base of each of the detachable valves is formed of a silicon elastomer and wherein the lubricant is silicone based.

26. In a system for artificial vessel embolization, a catheter adapted to be inserted into the vessel and having a passage extending therethrough, a balloon delivery catheter slidably mounted in the passage in the first-named catheter, the balloon delivery catheter comprising a flexible elongate element having proximal and distal extremities, a detachable balloon detachably secured to the distal extremity of the flexible elongate element, means carried by the proximal extremity of the flexible elongate element permitting inflation and deflation of a detachable balloon, an introducer catheter receiving said first named catheter, said introducer catheter including a flexible link having a smooth surface passage extending therethrough, and clamping means carried by the introducer catheter for clamping off the smooth surface passage in the introducer catheter.

* * * * *